United States Patent [19]

Minokami et al.

[11] Patent Number: 5,326,488
[45] Date of Patent: Jul. 5, 1994

[54] MANNICH REACTION PRODUCT AND PROCESS FOR PRODUCING THE SAME AND USE OF THE PRODUCT

[75] Inventors: Tomiyasu Minokami; Hiroaki Koshima; Hirotaka Yamasaki, all of Sodegaura; Masahisa Gotoh, Ichihara, all of Japan

[73] Assignee: Idemitsu Kosan Co., Ltd., Tokyo, Japan

[21] Appl. No.: 16,232

[22] Filed: Feb. 11, 1993

[30] Foreign Application Priority Data

Feb. 18, 1992 [JP] Japan .................................. 4-030840

[51] Int. Cl.$^5$ ................. C10M 135/30; C10M 151/04
[52] U.S. Cl. ................... 252/47.5; 252/46.3; 252/49.6; 548/547
[58] Field of Search ............................ 252/47.5, 46.3; 548/547

[56] References Cited

U.S. PATENT DOCUMENTS

| | | | |
|---|---|---|---|
| 4,178,259 | 12/1979 | King | 252/47.5 |
| 4,440,655 | 4/1984 | Gemmill, Jr. et al. | 252/47.5 |
| 4,450,102 | 5/1984 | Lindstrom et al. | 548/547 |
| 4,587,026 | 5/1986 | Horodysky | 252/46.3 |
| 5,156,757 | 10/1992 | Migdal et al. | 252/47.5 |
| 5,166,439 | 11/1992 | Lam et al. | 252/47.5 |

FOREIGN PATENT DOCUMENTS

| | | |
|---|---|---|
| 0270710 | 6/1988 | European Pat. Off. . |
| 0311318 | 4/1989 | European Pat. Off. . |
| 0454380 | 10/1991 | European Pat. Off. . |
| 1559643 | 3/1969 | France . |
| 993484 | 5/1965 | United Kingdom . |

OTHER PUBLICATIONS

Database WPI, Derwent Publications Ltd., AN 76-17862X, JP-A-51 008 304, Jan. 23, 1976.

Primary Examiner—Ellen M. McAvoy
Attorney, Agent, or Firm—Oblon, Spivak, McClelland, Maier & Neustadt

[57] ABSTRACT

Disclosed is a substance useful as a detergent-dispersant which has excellent stability at high temperatures and has an oxidation stability, a detergent-dispersant containing the same, a process of producing it, and fuel oil and lubricating oil composition comprising it.

12 Claims, No Drawings

MANNICH REACTION PRODUCT AND PROCESS FOR PRODUCING THE SAME AND USE OF THE PRODUCT

BACKGROUND OF THE INVENTION

1. Field of the Invention

The present invention relates to a Mannich reaction product and a process for producing the same and the use of the product, and particularly relates to a Mannich reaction product useful as a detergent-dispersant for lubricants, a process for producing the same, a detergent-dispersant containing said product, and a lubricating oil composition containing said detergent-dispersant. 2. Description of the Related Arts Generally, conventional ash-free type detergent-dispersants including succinimide-based ones and hydroxybenzylamine-based ones, have been used extensively as additives for gasoline, diesel-engine oils, being valued highly for their remarkable actions of dispersing fine particles. These are regarded as very important additives for lubricants, because they have synergistic effects with dialkyl zinc dithiophosphate or metal-type detergent-dispersants. Recently, however, their insufficient stability at high temperature have often been pointed out.

Japanese Patent Publication No. 43631/1971 discloses, as an ash-free type detergent-dispersant stable against oxidation having an improved oil-solubility, a reaction product obtained by reacting the reaction intermediate of alkylphenol, formaldehyde, and polyalkylene polyamine with alkenyl succinic arthydride, or a reaction product obtained by reacting the thus resulting product with a boron-containing compound. Japanese Patent Application Laid-Open No. 8304/1976 discloses a reaction product obtained by reacting the reaction intermediate of alkenyl (snhydrous) succinic acid and polyalkylene polyamine, in the presence of aidehyde, with an aromatic alcohol (for example, alkylphenol, phenol, and thiodiphenol). Also these reaction products, however, are insufficient in stability at high temperature.

Further, Japanese Patent Application Laid-Open No. 168492/1988 discloses a reaction product obtained by reaction with a glycolic acid in place of the boron-containing compound described in Japanese Patent Publication No. 43631/1971, but it is insufficient in stability at high temperature, also.

Conventional lubricating oils for internal-combustion engine comprise a base oil, an ash-free type detergent-dispersant such as polybutenyl succinimide, and metal-type detergent-dispersant such as sulfonate and phenates of alkaline earth metals, and anti-wear agents such as alkyl zinc dithiophosphate. The metal contents in the components of additives are combined with oxides and sulfates by combustion, which might be responsible for environmental pollution.

In recent years, among the internal-combustion engines, particularly in diesel engines, measures to counter the environmental pollution by inhibiting particulates and NOx in exhaust gas have become important subject. To counter the environmental pollution, exhaust gas purifiers such as particulate traps and exhaust gas removing catalysts are used, but these means do not prevent blockage of the system by metal oxides or sulfides resulted from combustion by the use of conventional lubricating oils for internal combustion engine. In this regard, there rose the need for a lubricating oil for internal combustion engine which can reduce the blocking by these metal oxides or sulfides to as little as possible.

In order to meet this need, Japanese Patent Application Laid-Open No. 163294/1989 discloses an ash-free type lubricating oil composition for internal combustion engine including diesel engines, comprising a conventional ash-free type detergent-dispersant, sulfurized alkylphenol and a metal deactivator. Although the composition has the feature of being ash-free, it has insufficient stability at high temperatures.

The present inventors have made researches to dissolve the defects in the prior arts as described above, and develop a substance useful as a detergent-dispersant being excellent in stability at high temperature and having a stability against oxidation.

The present inventors found that a reaction product having excellent stability at high temperatures by using a specific sulfurized alkylphenol in place of the aromatic alcohol described in Japanese Patent Publication No. 43631/1971 and Japanese Patent Application Laid-Open No. 8304/1976. The present invention has been accomplished basing on this finding.

SUMMARY OF THE INVENTION

The present invention provides a Mannich reaction product obtained by reacting alkenyl succinic acid or alkenyl succinic arthydride, polyamine, aldehyde and sulfurized alkylphenol represented by the general formula ( I ):

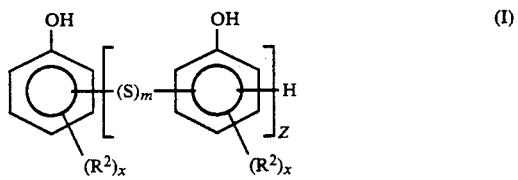

wherein $R^2$ indicates an alkyl group having 4 to 25 carbon atoms, m indicates an integer of 1 to 8, x indicates 1 or 2, and z indicates an integer of 1 to 9; and a Mannich reaction product obtained by reacting alkenyl succinic acid or alkenyl succinic anhydride, and polyamine, aidehyde, sulfurized alkyl phenol represented by the general formula (I) , and a boron-containing compound; and a detergent-dispersant containing these Mannich reaction products.

The present invention also provides a process for producing a Mannich reaction product characterized by reacting 1 mol or more of sulfurized alkylphenol represented by the general formula (I) to 1 mol of polyamine in the production of said Mannich reaction product.

DESCRIPTION OF THE PREFERRED EMBODIMENTS

The reaction product according to the present invention is a reaction product obtained by reacting (a) alkenyl succinic acid or alkenyl succinic arthydride,
(b) polyamine,
(c) sulfurized alkylphenol, and
(d) aidehyde
in a molar ratio of (a):(b):(c):(d)=1~10:1:1~10:1~ 10, preferably in a ratio of 1~2:1:1~2:1~5.

The reaction products of the present invention include, as mentioned above, two kinds. One of them is a reaction product obtained by reacting the intermediate resulted from reacting (a) and (b) above with (c) in the presence of (d) (this method is referred to as Method A).

The other is a reaction product obtained by reacting the intermediate resulting from reacting (c), (d) and (b) mentioned above with (a) (this method is referred to as Method B).

The reaction of (a) and (b) in Method A is performed at about 100° to 250° C., preferably about 150° to 200° C. In the reaction, a solvent, for example, an organic solvent such as hydrocarbon oil can be used. The reaction of the resulting intermediate with (c) in the presence of (d) is performed at about 0° to 200° C., preferably about 50° to 150° C.

The reaction of (c), (d) and (b) in Method B is performed at about 0° to 200° C., preferably about 50° to 150° C. The reaction of the resulting intermediate and (a) is performed at about 100° to 250° C., preferably about 150° to 200° C.

In order to explain the above reaction in more detail, an example is shown below in which polyalkenyl succinic anhydride, polyethylene polyamine, and formaldehyde are used as (a) alkenylsuccinic acid or alkenyl succinic anhydride, (b) polyamine, and (d) aidehyde, respectively.

In Method A, an alkenyl succinic anhydride as component (a), represented by the general formula (II):

$$R^1-CH-CO\diagdown O \diagup CH_2-CO \quad (II)$$

wherein $R^1$ shows a group of a polymer or copolymer drived from an olefin having 2 to 20 carbon atoms, or mixed group thereof, is reacted with a polyethylene polyamine as component (b) represented by the general formula (III):

$$H_2N(CH_2CH_2NH)_nH \quad (III)$$

wherein n shows an integer of 1 to 6, and the resulting alkenyl mono-succinimide represented by the general formula (IV):

$$R^1-CH-CO\diagdown N(CH_2CH_2NH)_nH \diagup CH_2-CO \quad (IV)$$

wherein $R^1$ and n are as defined before, and/or he alkenyl bis-succinimide represented by the general formula (V):

$$R^1-CH-CO\diagdown N(CH_2CH_2NH)_{n-1}CH_2CH_2N \diagup CO-CH-R^1 \diagdown CH_2-CO \quad CO-CH_2 \quad (V)$$

wherein $R^1$ and n are as defined before, are reacted with (d) formaldehyde and a sulfurized alkylphenol as component (c) represented by the general formula (I).

In this case, the product of reaction with alkenyl mono-succinimide is mannich sulfurized alkylphenol coupled alkenyl mon-succinimide product which comprises a constitutional structure unit represented by the general formula (VI):

$$\text{(VI) structure: OH-phenyl-(S)}_m\text{-phenyl-OH with }(R^2)_x\text{ substituents, }z\text{ repeating}$$

wherein $R^2$, m, x and z are as defined before, coupled with, per benzene nucleus, one or two constitutional units represented by the general formula (VII):

$$\left[R^1-CH-CO\diagdown N(CH_2CH_2NH)_n-CH_2 \diagup CH_2-CO\right] \quad (VII)$$

wherein $R^1$ and n are as defined above.

The product of reaction with alkenyl bis-succinimide is Mannich sulfurized alkylphenol coupled alkenyl bis-succinimide product which comprises the constitutional unit represented by the general formula (VI) coupled with, per benzene nucleus, one or two constitutional units represented by the general formula (VIII)

$$\left[R^1-CH-CO\diagdown N(CH_2CH_2NH)_{n-2}CH_2CH_2N-CH_2 \diagup CH_2-CO \quad CH_2CH_2N\diagup CO-CH-R^1 \diagdown CO-CH_2\right] \quad (VIII)$$

wherein $R^1$ and n are as defined before.

On the other hand, in Method B, formaldehyde, a sulfurized alkylphenol represented by the general formula (I), and a polyethylene polyamine represented by the general formula (III) are reacted to produce a compound which comprises a constitutional unit of the above-mentioned general formula (VI) coupled with, per benzene nucleus, one or two constitutional units of the general formula (IX):

$$[NH_2(CH_2CH_2NH)_n-CH_2]- \quad (IX)$$

With the above compound, the alkenyl succinic arthydride represented by the general formula (II) is further reacted to obtain a Mannich sulfurized alkylphenol coupled mono-alkenylsuccinimide which comprises the constitutional unit represented by the general formula (VI) coupled with, per benzene nucleus, one or two structural units represented by the aforegoing general formula (VII).

The alkenyl group $R^1$ of alkenyl succinic acid or alkenyl succinic anhydride as component (a) to be used in the above reaction has a weight average molecular weight (Mw) of about 200 to 4000, preferably about 600 to 2000, and is derived from polymer or copolymer of monoolefin or diolefin having 2 to about 20 carbon atoms such as ethylene, propylene, butene, butadiene, decene, or hexadecene, or mixtures thereof, maleic acid or maleic anhydride, and may be produced by the known methods.

As polyamines as component (b), mentioned are primary amines or secondary amines, which are usually compounds represented by the general formula (X):

In the formula, a is an integer of 1 to 8, preferably 3 to 6, and b is 0 to 1. $R^4$ is a hydrogen, an alkyl group, an aralkyl group, a cycloalkyl group, an aryl group, an alkaryl group, an alkenyl group or, when deactively substituted, a hydrocarbon group comprising an alkynyl group containing such a group. When $R^4$ is an alkyl group, it is usually methyl, ethyl, n-propyl, isopropyl, n-butyl, isobutyl, sec-butyl, amyl, octyl, decyl, or octadecyl. When $R^4$ is an aralkyl group, it usually is benzyl, or β-phenylethyl. When $R^4$ is a cycloalkyl group, it usually is cyclohexyl, cycloheptyl, cyclooctyl, 2-methylcycloheptyl, 3-butylcyclohexyl, or 3-methylcyclohexyl. When $R^4$ is an aryl group, it usually is phenyl, or naphthyl. When $R^4$ is an alkaryl group, it usually is tolyl, or xylyl. When $R^4$ is an alkenyl group, it usually is vinyl, allyl, or 1-butenyl. When $R^4$ is an alkynyl group, it usually is ethynyl, propynyl, or butynyl.

$R^4$ may be deactively substituted, that is, $R^4$ may contain a nonreactive substituent such as alkyl, aryl, cycloalkyl, ether, halogen, and nitro. As $R^4$ group deactively substituted, usually 3-chloropropyl, 2-ethoxyethyl, carboethoxymethyl, 4-methylcyclohexyl, p-chlorophenyl, p-chlorobenzyl, 3-chloro-5-methylphenyl and the like are mentioned. Preferred $R^4$ groups are alkyl groups, that is, alkyl groups having 1 to 10 carbon atoms, for example, groups including methyl, ethyl, n-propyl, isopropyl, butyls, amyls, hexyls, octyls, and decyls. $R^4$ is most preferably a hydrogen.

In accordance with the fact that $R^3$ is divalent and indicates other than hydrogen, $R^3$ is a hydrocarbon group selected from the identical group to $R^4$. Preferably $R^4$ is a hydrogen, and $R^3$ is —$CH_2CH_2$—. Amines to be used are usually as follows.

propylenediamine (PDA)
diethylenetriamine (DETA)
triethylenetetramine (TETA)
tetraethylenepentamine (TEPA)
pentaethylenehexamine (PEHA)

The sulfurized alkylphenyl as component (c) is usually represented by the general formula (I) as mentioned before. In that formula, m is 1 to about 8, preferably 1 to about 2, z is 1 to about 9, preferably 1 to about 3. x is 1 to 2, preferably 1. $R^2$ is a hydrocarbon group having about 4 to 25 carbon atoms, preferably about 8 to 22 carbon atoms, for example, an alkyl group, an alkenyl group, and an aralkyl group, more specifically, a hydrocarbon group such as butyl, amyl, hexyl, octyl, nonyl, decyl, dodecyl, and hexadecyl, or groups derived from petroleum hydrocarbons such as liquid paraffin, wax, olefin polymer (polyethylene, polypropylene, polybutene and the like), or mixed groups thereof.

Sulfurized alkylphenols to be used therein usually are those derived from alkylphenols shown below, sulfurs and the like, and may be produced by the known methods.

p-t-butylphenol
octylphenol
nonylphenol
dodecylphenol
hexadecylphenol
eicocylphenol The aldehyde as component (d) is usually represented by the general formula (XI):

In the formula, $R^5$ is a hydrogen, an alkyl group, an aralkyl group, a cycloalkyl group, an aryl group, an alkaryl group, an alkenyl group or, when deactively substituted, a hydrocarbon group comprising an alkynyl group containing such a group. When $R^5$ is an alkyl group, it usually is methyl, ethyl, n-propyl, isopropyl, n-butyl, isobutyl, sec-butyl, amyl, octyl, decyl, octadecyl, or the like. When $R^5$ is an aralkyl group, it usually is benzyl, β-phenylethyl or the like. When $R^5$ is a cycloalkyl group, it usually is cyclohexyl, cycloheptyl, cyclooctyl, 2-methylcycloheptyl, 3-butylcyclohexyl, 3-methylcyclohexyl, or the like. When $R^5$ is an aryl group, it usually is a phenyl, naphthyl or the like. When $R^5$ is an alkaryl group, it usually is tolyl, xylyl or the like. When $R^5$ is an alkenyl group, it usually is vinyl, allyl, 1-butenyl or the like. When $R^5$ is an alkynyl group, it usually is ethynyl, propynyl, butynyl or the like.

$R^5$ may be deactively substituted, that means, may contain a nonreactive substituent such as alkyl, aryl, cycloalkyl, ether, halogen, and nitro. As deactively substituted $R^5$, usually 3-chloropropyl, 2-ethoxyethyl, carboethoxymethyl, 4-methylcyclohexyl, p-chlorophenyl, p-chlorobenzyl, 3-chloro-5-methylphenyl and the like are mentioned. Preferable $R^5$ is a halogen or an alkyl group, that is, alkyl group having 1 to 10 carbon atoms, for example, groups such as methyl, ethyl, n-propyl, isopropyl, butyls, amyls, hexyls, octyls, decyls and the like. $R^5$ is most preferably a hydrogen.

Aldehyde to be used therein are specifically, formaldehyde, paraformaldehyde, ethanal, propanal, butanal and the like.

The Mannich sulfurized alkylphenol coupled alkenyl monosuccinimide or bis-succinimide obtained by the above-mentioned reaction is useful as a detergent-dispersant, and has a stability against oxidation, and particularly has an excellent stability at high temperatures. That is, a detergent-dispersant comprising these reaction products can be provided.

Further, another reaction product according to the present invention is obtained by reacting (e) boron-containing compound with the above-mentioned components (a) to (d) with (b) polyamine, preferably in a molar ratio of (b):(e)=1:0.05~10, more preferably 1:0.2~2. Said reaction product can be obtained by reacting the product resulting from the reaction of above-mentioned components (a) to (d) with component (e), or by reacting the foregoing polyalkenyl succinimide or bis-succinimide with component (e), and after that, reacting aidehyde and sulfurized alkylphenol represented by the general formula (I).

The detergent-dispersant comprising said reaction product has a stability against oxidation, particularly has very remarkable stability at high temperatures, and has been improved in co-existence ability with other additives.

The above-mentioned reaction with (e) is performed at about 50° to 250° C., preferably about 100° to 200° C. In performing the reaction, a solvent, for example, an organic solvent such as hydrocarbon oil can be used. 1.5 atoms at most of boron can be reacted per 1 atom of nitrogen, but the ratio of boron to nitrogen (B/N) is preferably in the range of 0.05 to 1.0, and (B/N) ratio by weight is more preferably in the range of 0.1 to 0.5.

As (e) the boron-containing compound, boron oxide, halogenated boron, boric acid, boric arthydride, and boric acid ester, for instance, can be used.

The Mannich reaction product obtained in the above reaction can be effectively used as a detergent-dipersant. Said detergent-dispersant can also be compounded with hydrocarbon oil or synthetic oils as a lubricataing oil base in a ratio of about 0.1 to 80% by weight to prepare a lubricating oil composition. The preferred amount of the detergent-dispersant to be compounded is in the range of about 0.5 to 20% by weight. Said detergent-dispersant can also be added to hydrocarbon oils used as fuel oil.

As the hydrocarbon oil herein, either fraction of fuel oils such as gasoline, kerosene, and light oil, or lubricating oil (for example, paraffin-based mineral oil, naphthene-based mineral oil, and aromatic mineral oil) can be used, and those purified through whatever purifying method such as solvent purification, hydrogenation purification, and hydrocracking can be used. As the synthetic oils, polyphenylether, alkylbenzene, alkylnaphthalene, ester-based, glycol-based or polyolefin-based synthetic oils can be used. Kinematic viscosity at 100° C. of lubricating oil fraction is in the range of 1 to 50 cSt, preferably 3 to 10 cSt.

As the ester-based synthetic oils, synthetic oils comprising ester of monobasic acid or dibasic acid and alcohol, for example, ester obtained by reacting a dibasic acid having about 6 to 16 carbon atoms and a straight chain or branched alcohol having about 5 to 20 carbon atoms can be used. Particularly, adipic acid ester, cebacic acid ester, azeleic acid ester, trimethylol propane ester, trimethylol ethane ester, pentaerythritol ester, and neopentylglycol ester are preferable. As polyolefin-based synthetic oils, purificated liquid by low polymerization or copolymerization of low olefins such as ethylene, propylene, butylene, octene, decene, and dodecene, and mixtures thereof, or oils obtained by hydrogenation purification of them are suitably used. Moreover, complexed esters comprising dibasic acid, glycol and monobasic acid can also be used.

A fuel oil of hydrocarbon comprising the above-mentioned detergent-dispersant can be used as a detergent to prevent the impurities from adhering to the carbureter of an internal combustion engine and to remove the adhering impurities.

Further, hydrocarbon oil or lubricating oil fraction of synthetic oil or mixture thereof comprising the above-mentioned detergent-dispersant can be used as lubricating oil composition for internal combustion engines (for example, lubricating oil composition for diesel engine), gear oil, bearing oil, transmission oil, shock absorber oil, and lubricating oil for industrial use.

In the present invention, antioxidant, antiwear agent, viscosity index improver, pour point depressant and other additives to be compounded usually in lubricating oils can be used, and do not inhibit the action of the detergent-dispersant of the present invention.

As described above, the Mannich reaction product of the present invention has stability against oxidation, and particularly, exhibits stability at high temperatures which is three times better than that of conventional product, and is useful as an excellent detergent-dispersant for hydrocabon oil and for synthetic oil.

Consequently, the Mannich reaction product of the present invention can be extensively utilized, and has a very great practical value.

The present invention will be explained in greater detail with reference to the following reference examples, examples and comparative examples, but the present invention is not limited thereto.

Preparation example of sulfurized alkylphenol is shown as a reference example.

Reference Example 1 (Preparation of Sulfurized Hexadecylphenol 1)

In a 1-liter (L) flask, 319 g (1 mol) of hexadecylphenol obtained by reacting phenol with straight chain 1-hexadecene, 16 g (0.5 mol) of sulfur, 37 g (0.5 mol) of calcium hydroxide, and 31 g (0.5 mol) of ethylene glycol were placed, and reacted at 135° C. in a nitrogen stream for 4 hours. Then, the reaction system was heated to 160° C., unreacted ethylene glycol and the resulting water were vacuum-distilled away, and the residue was cooled to 40° C. 500 ml of hexane was added thereto, and the mixture was neutralized with 4N chloric acid. The hexane solution was washed with water, and hexane and unreacted hexadecylphenol were vacuum-distilled away.

The result by field release ionization mass spectrometry shows that the resulting sulfurized hexadecylphenol (yield: 170 g) is a mixture of compounds represented by general formula (I) wherein m is 1 to 3, z is 1 to 3, and $(z=1):(z=2):(z=3)=84:13:2$, having a sulfur content of 5.10% by weight.

Reference Example 2 (Preparation of Sulfurized Hexadecylphenol 2)

In a 1-L flask equipped with a nitrogen introduction tube, and a nitrogen discharge tube connected to a hydrogen chloride scrubber, 319 g (1 mol) of hexadecylphenol and 200 g of hexane were placed, and stirred so as to be homogeneous. While nitrogen was blown through a rate of 100 ml/min, 41 g (0.3 mol) of sulfur monochloride was added over about 30 minutes at room temperature, and the mixture was reacted for 2 hours. Then hexane and unreacted hexadecylphenol were vacuum distilled away.

The result of peak intensity ratio by the field release ionization mass spectrometry shows that the resulting sulfurized hexadecylphenol (yield: 264 g) was a mixture of compounds wherein m is 1 to 3, z is 1 to 3, and $(z=1):(z=2)=92:8$, having a sulfur content of 4.94% by weight. Reference Example 3 (Preparation of Sulfurized Alkylphenol having 20 to 22 Carbon Atoms)

The reaction of Reference Example 2 was repeated except that 389 g (1 mol) of a mixture of alkylphenol obtained by reacting phenol and straight chain 1-eicosene and 1-dococene was used in place of hexadecylphenol. The yield of sulfurized alkylphenol without performing distillation purification was 403 g, wherein sulfur content was 4.88% by weight:

Reference Example 4 (Preparation of Sulfurized Dodecylphenol (Straight Chain))

The reaction of Example 1 was repeated except that 262 g (1 mol) of dodecylphenol obtained by reacting phenol and straight chain 1-dodecene was used in place of hexadecylphenol. The yield of resulting sulfurized dodecylphenol (sraight chain) was 214 g, wherein sulfur content was 7.22% by weight.

Reference Example 5 (Preparation of Sulfurized Dodecylphenol (Branched))

The reaction of Reference Example 1 was repeated except that 262 g (1 mol) of dodecylphenol obtained by reacting phenol and dodecene, which is the tetramer of propylene, was used in place of hexadecylphenol. The yield of the resulting sulfurized dodecylphenol (branched) was 213 g, wherein sulfur content was 7.28% by weight.

Reference Example 6 (Preparation of Sulfurized Nonylphenol)

The reaction of Reference Example 1 was repeated except that 221 g (1 mol) of nonylphenol obtained by reacting phenol and nonene, which is the trimer of propylene, was used in place of hexadecylphenol. The yield of the resulting sulfurized nonylphenol was 179 g, wherein sulfur content was 8.41% by weight.

Reference Example 7 (Preparation of Sulfurized Phenol)

The reaction of Reference Example 1 was repeated except that 94 g (1 mol) of phenol was used in place of hexadecylphenol. The yield of the resulting sulfurized phenol was 76 g, wherein sulfur content was 24.6% by weight.

Reference Example 8 (Preparation of Sulfurized Alkylphenol having 26 to 28 Carbon Atoms)

The reaction of Reference Example 2 was repeated except that 473 g (1 mol) of alkylphenol obtained by reacting phenol and straight chain 1-hexacosene and 1-octacosene was used in place of hexadecylphenol. The yield of the sulfurized alkylphenol obtained without distillation purification was 480 g, wherein sulfur content was 3.72% by weight.

Example 1

In a 1-L autoclave, 1100 g of polybutene (Mw: 987), 6.4 g (0.021 mol) of cetyl boromide, and 115 g (1.2 mol) of maleic arthydride were placed, the atmosphere in the reaction system was substituted with nitrogen, and the mixture was reacted at 240° C. for 5 hours. Then the temperature in the system was cooled to 215° C., unreacted maleic arthydride and cetyl boromide were vacuum distilled away, and the residue was cooled to 140° C. and filtered. The yield of the resulting polybutenyl succinic anhydride was 1099 g, and the saponification value of it was 80 mg KOH/g.

In a 2-L separable flask, 500 g of the resulting polybutenyl succinic arthydride, 64 g (0.34 mol) of tetraethylene pentamine (TEPA), and 300 g of mineral oil were placed, and reacted at 150° C. in a stream of nitrogen for 2 hours. Then temperature of the reaction system was raised to 200° C., unreacted TEPA and resulting water were vacuum distilled away, and the residue was cooled to 140° C. and filtered. The yield of the resulting polybutenyl succinimide was 784 g, of which base number was 78 mg KOH/g and kinematic viscosity at 100° C. was 147 cSt.

In a 500 -ml separable flask, 104 g of the resulting polybutenyl succinimide, 37.1 g of sulfurized hexadecylphenol produced in Reference Example 1, and 3.5 g (0.116 mol) of paraformaldehyde were placed, and reacted at 120° C. for 4 hours, and further at 160° C. for 1 hour. The unreacted paraformaldehyde and the resulting water were vacuum distilled away at 160° C., and the residue was cooled to 140° C. and filtered. The yield of the resulting reaction product was 127 g. The properties of the reaction product are shown in Table 1.

Example 2

The reaction of Example 1 was repeated except that in a 500-ml separable flask, 107 g of polybutenyl succinimide (the ratio of polybuenyl succinimide and tetraethylenepentamine is shown in Table 3. The rest is mineral oil.) as obtained in Example 1, 35.7 g of sulfurized hexadecylphenol as prepared in Reference Example 2 and 3.4 g (0.113 mol) of paraformaldehyde were used. The yield of the resulting reaction product was 129 g. The properties of the reaction product are shown in Table 1.

Example 3

The reaction of Example 2 was repeated except that 45.4 g of sulfurized alkylphenol having 20 to 22 carbon atoms as obtained in Reference Example 3 were used. The yield of the resulting reaction product was 128 g. The properties of the reaction product are shown in Table 1.

Example 4

The reaction of Example 2 was repeated except that 30.5 g of sulfurized dodecylphenol (straight chain) as obtained in Reference Example 4 was used. The yield of the resulting reaction product was 113 g. The properties of the reaction product are shown in Table 1.

Example 5

The reaction of Example 2 was repeated except that 30.5 g of sulfurized dodecylphenol (branched) as obtained in Reference Example 5 was used. The yield of the resulting reaction product was 112 g: The properties of the reaction product are shown in Table 1.

Example 6

The reaction of Example 2 was repeated except that 25.1 g of sulfurized nonylphenol as obtained in Reference Example 6 was used. The yield of the resulting reaction product was 107 g. The properties of the reaction product are shown in Table 1.

Example 7

The reaction of Example 1 was repeated except that 914 g of polybutene (Mw: 800 ) was used in place of polybutene (Mw: 987). The yield of the resulting polybutenyl succinic arthydride was 943 g, and the saponification value was 95 mg KOH/g.

Subsequently, 500 g of the resulting polybutenyl succinic arthydride, 76.1 g (0.40 mol) of TEPA, and 300 g of mineral oil were used to conduct the same reaction as in Example 1. The yield of the resulting polybutenyl succinimide was 812 g, the saponification value was 85 mg KOH/g, and the kinematic viscosity at 100° C. was 107 cSt.

Further, the reaction of Example 1 was repeated except that 107 g of the resulting polybutenyl succinimide, 37.5 g of sulfurized hexadecyl phenol as obtained in Reference Example 2 and 3.4 g (0.113 mol) of paraformaldehyde were used. The yield of the resulting reaction product was 130 g. The properties of the reaction product are shown in Table 1.

Example 8

The reaction of Example 1 was repeated except that 890 g of polybutene (Mw: 445) in place of polybutene (Mw: 987), 11 g (0.036 mol) of cetyl bromide, and 397 g (2.1 mol) of maleic arthydride were used. The yield of the resulting polybutenyl succinic arthydride was 991 g and the saponification value was 141 mg KOH/g.

Subsequently, 500 g of the resulting polybutenyl succinic arthydride, 113 g (0.60 mol) of TEPA, and 300 g of mineral oil were used to conduct the same reaction as in Example 1. The yield of the resulting polybutenyl succinimide was 847 g, of which basic value of it was 125 mg KOH/g and kinematic viscosity at 100° C. was 140 cSt.

Further, the reaction of Example 1 was repeated except that 107 g of the resulting polybutenyl succinimide, 59.0 g of sulfurized hexadecylphenol as obtained in Reference Example 2, and 3.4 g (0.113 mol) of paraformaldehyde were used. The yield of the resulting reaction product was 143 g. The properties of the reaction product are shown in Table 1.

Example 9

In a 1-L separable flask, 237 g of the polybutenyl succinimide as obtained in Example 1 and 28.0 g of boric acid were placed, and reacted for 4 hours at 150° C. in a stream of nitrogen. The resulting water was vacuum-distilled away at 150° C., and the residue was cooled to 140° C. and filtered. The yield of the resulting reaction product was 238 g, and the base number was 61 mg KOH/g.

In a 500-ml separable flask, 111 g of the resulting boron-based polybutenylsuccimide, 35.7 g of sulfurized hexadecylphenols prepared in Reference Example 2, and 3.4 g (0.113 mol) of paraformaldehyde were placed, and reacted for 4 hours at 120° C., and further one hour at 160° C. At 160° C., the unreacted paraformaldehyde and the resulting water were vacuum-distilled away, and the residue was cooled to 140° C. and filtered. The yield of the resulting reaction product was 125 g. The properties of the reaction product are shown in Table 1.

Example 10

In a 1-L autoclave, 240 g of polydecene (Mw: 2038), 0.9 g (0.003 mol) of cetyl boromide, 63 g (0.64 mol) of maleic anhydride were placed, the atmosphere in the system was substituted with nitrogen, and the mixture was reacted at 248° C. for 5 hours. Then, the mixture was cooled to 215° C., unreacted maleic arthydride and cetyl boromide were vacuum distilled away, and the residue was cooled to 140° C. and filtered. The yield of the resulting polydecenyl succinic anhydride was 217 g, and the saponification value of it was 42 mg KOH/g.

In a 1-L separable flask, 200 g of the resulting polybutenyl succinic anhydride, 13 g (0.07 mol) of TEPA, and 105 g of minearl oil were placed, and reacted at 150° C. in a stream of nitrogen for 2 hours. Then the temperature of the system was raised to 200° C., unreacted TEPA and the resulting water were vacuum-distilled away, and the residue was cooled to 140° C. and filtered. The yield of the resulting polydecenyl succinimide was 266 g, of which the base number was 41 mg KOH/g and the kinematic viscosity at 100° C. was 32 cSt.

In a 500-ml separable flask, 225 g of the resulting polydecenyl succinimide, 40 g of the sulfurized hexadecylphenol prepared in Reference Example 1 and 3.8 g (0.125 mol) of paraformaldehyde were placed, and reacted at 120° C. for 4 hours, and then at 160° C. for one hour. At 160° C. unreacted paraformldehyde and the resulting water were vacuum-distilled away, and the residue was cooled to 140° C. and filtered. The yield of the resulting reaction product was 216 g. The properties of the reaction product are shown in Table 1.

Example 11

The reaction of Example 1 was repeated except that 909 g of polydecene (Mw: 909) in place of polybutene (Mw: 987), 5.5 g (0.018 mol) of cetyl boromide, and 103 g (1.05 mol) of maleic anhydride were used. The yield of the resulting polydecenyl succinic arthydride acid was 937 g, and the saponification value of it was 60 mg KOH/g.

Subsequently, 500g of the resulting polydecenyl succinic anhydride, 50.5 g (0.267 mol) of TEPA, and 300 g of mineral oil were used to conduct the reaction as in Example 1. The yield of the resulting polydecenyl succinimide was 782 g, of which the base number was 52 mg KOH/g and the kinematic viscosity at 100° C. was 48 cSt.

Further, the reaction of Example 1 was repeated except that 107 g of the resulting polydecenyl succinimide, 41.6 g of sulfurized hexadecylphenol as obtained in Reference Example 2, and 4.0 g (0.132 mol) of paraformaldehyde were used. The yield of the resulting reaction product was 138 g. The properties of the reaction product are shown in Table 1.

Example 12

The reaction of Example 1 was repeated except that 1090 g of polydecene (Mw: 545) in place of polybutene (Mw: 987), 11 g (0.036 mol) of cetyl boromide, and 397 g (2.1 mol) of maleic anhydride were used. The yield of the resulting polydecenyl succinic arthydride was 1153 g, and the saponification value was 116 mg KOH/g.

Subsequently, 500 g of the resulting polydecenyl succinic anhydride, 98 g (0.519 mol) of TEPA, and 300 g of mineral oil were used to conduct the reaction as in Example 1. The yield of the resulting polydecenyl succinimide was 814 g, of which the base number was 77 mg KOH/g, and the kinematic viscosity at 100° C. was 67 cSt.

Further, the reaction of Example 1 was repeated except that 107 g of the resulting polydecenyl succinimide, 59.1 g of sulfurized hexadecylphenol as obtained in Reference Example 2, and 5.6 g (0.187 mol) of paraformaldehyde were used. The yield of the resulting reaction product was 153 g. The properties of the reaction product are shown in Table 1.

Example 13

The reaction of Example 2 was repeated except that 71.4 g of the sulfurized hexadecylphenol as obtained in Reference Example 2 was used. The yield of the resulting reaction product was 156 g. The properties of the reaction product are shown in Table 1.

Example 14

In a 500-ml separable flask, 9.4 (0.05 mol) of TEPA was placed, and 3.4 g (0.113 tool) of paraformaldehyde was added thereto. Further, 35.7 g of sulfurized hexadecylphenol obtained in Reference Example 2 was added, and the mixture was reacted at 120° C. for 4 hours. The temperature of the reaction system was raised to 140° C., and the light fraction was vacuum-distilled away. 69.9 g (0.053 mol) of polybutenyl succinic anhydride and 37.1 g of mineral oil were added to the residue, and the mixture was reacted for 2 hours at 140° C., and further one hour at 160° C. Then, the light fraction was vacuum-distilled away at 160° C., and then the residue was cooled to 140 ° C. and filtered. The yield of the resulting reaction product was 120 g. The properties of the reaction product are shown in Table 1.

Comparative Example 1

The polybutenyl succinimide itself as obtained in Example 1 was used as a detergent-dispersant. The properties of the reaction product are shown in Table 1.

Comparative Example 2

The reaction of Example 1 was repeated except that 15.9 g (0.05 mol) of hexadecylphenol was used in place of sulfurized hexadecylphenol. The yield of the resulting reaction product was 108 g. The properties of the reaction product are shown in Table 1.

Comparative Example 3

The reaction of Example 1 was repeated except that 10.9 g (0.05 mol) of sulfurized phenol as obtained in Reference Example 6 was used in place of sulfurized hexadecylphenol. The yield of the resulting reaction product was 81 g. The properties of the reaction product are shown in Table 1.

Comparative Example 4

The reaction of Example 1 was repeated except that 4.7 g (0.05 mol) of phenol was used in place of sulfurized hexadecylphenol. 7.6 g (0.1 mol) of glycol acid was added to the resulting reaction product, and the mixture was reacted at 160° C. for 4 hours in a stream of nitrogen, the resulting water was distilled away, and the residue was cooled to 140° C. and filtered. The yield of the resulting reaction product was 94 g. The properties of the reaction product are shown in Table 1.

Comparative Example 5

The reaction of Example 2 was repeated except that 55.5 g of sulfurized alkylphenol having 26 to 28 carbon atoms as prepared in Reference Example 7 was used. The yield of the resulting reaction product was 108 g. The properties of the reaction product are shown in Table 1.

Comparative Example 6

The reaction of Example 2 was repeated except that 107 g of dodecenyl succinimide in place of polybutenyl succinimide, 112 g of sulfurized hexadecylphenol as obtained in Reference Example 2, and 10.7 g (0.355 mol) of paraformaldehyde were used. The yield of the reaction product was 193 g. The properties of the reaction product are shown in Table 1.

Comparative Example 7

In 500-ml separable flask, 37.6 g (0.2 mol) of TEPA was placed, and 13.6 g (0.452 mol) of paraformaldehyde was added thereto. Further, 142.8 g of sulfurized hexadecylphenol as obtained in Reference Example 2 was added, and the mixture was reacted for 4 hours at 120° C., and then one hour at 160° C. Subsequently, the light fraction was vacuum-distilled away at 160° C., and the residue was cooled to 140° C. and filtered. The yield of the resulting reaction product was 150 g. The properties of the reaction product are shown in Table 1.

Comparative Example 8

The reaction of Example 2 was repeated except that 17.9 g of sulfurized hexadecylphenol as obtained in Reference Example 2 was used. The yield of the resulting reaction product was 111 g. The properties of the reaction product are shown in Table 1.

The excellent properties of the detergent-dispersant of the present invention are proved by Hot Tube Test, Panel Coking Test, Oxidation Stability Test, and Low Temperature Apparent Viscosity Test. The results of the evaluation are shown in Table 2.

Tests of Examples 1 to 12 and Comparative Examples 1 to 7

In Hot Tube Test, Panel Coking Test and Oxidation Stability Test, with 95% by weight of 500 neutral fraction of mineral oil, and each 5% by weight of the detergent-dispersant of the above-mentioned Example or Comparative Example was compounded to make the test oil.

Therein, in Low Temperature Apparent Viscosity Test, with 90% by weight of 150 neutral fraction of mineral oil, and each 10% by weight of the detergent-dispersant of the above-mentioned Example or Comparative Example was compounded to make the test oils. The properties of the detergent-dispersant of the present invention according to the difference in production conditions are proved by the Test Example on Hot Tube Test, Panel Coking Test and Oxidation Stability Test. The ratios of the starting materials to be used and the results of the evaluation are shown in Table 3.

Tests of Examples 2, 13, and 14 and Comparative Example 8

The test oils were prepared in the same manner as in the above-mentioned Example 1.

Furthermore, it is proved by Test Examples by Hot Tube Test, Panel Coking Test, Oxidation Stability Test and Simple Diesel Engine Test that the lubricating oil composition of the present invention has an excellent properties as a lubricating oil composition for internal combustion engines. The results of the evaluation are shown in Table 4.

Test of Example 15

With 23% by weight of 150 neutral fraction of mineral oil and 65% by weight of 500 neutral faction of mineral oil, and 12% by weight of the detergent-dispersant as obtained in Example 9 was compounded to make a test oil.

Test of Example 9

In place of the detergent-dispersant of Example 9, 8.2% by weight of the boron-based polybutenyl succinimide of Example 9, 3.5% by weight of the sulfurized nonylphenol of Reference Example 5, and 0.3% by weight of 2.5-bis(nonyldithio)-1,3,4-thiadiazole were compounded to make the test oil.

Conditions for Tests are as follows.

Hot Tube Test

Into a glass tube with an inner diameter of 2 mm, test oil at a rate of 0.3 ml/hr, and air at 10 ml/min were blown for 16 hours while the temperature of the glass tube was maintained at 230° C. or 290° C. By comparison with the color sample, the color of lacquer adhering to the glass tube was evaluated marking 10 when it was transparent, and 0 when it was black. At the same time, the lacquer adhering to the inner wall of the glass tube was weighed.

Panel Coking Test

In accordance with Fed 791B Method 3462 (1969), the test was carried out under the conditions of panel temperature of 300° C., oil temperature of 100° C., for 3 hours.

Oxidation Stability Test

In accordance with JIS K 2514, the test was carried out at 165.5° C. for 48 hours. For Example 15 and Comparative Example 9, the test was carried out for 72 hours.

Low Temperature Apparent Viscosity Test

In accordance with JIS K 2215 4-15, the test was carried out at −20° C.

Simple Diesel Engine Test

With the use of 280 cc 1-cylindered engine manufactured by Yammer Diesel Co., Ltd., the period of durability up to lowering in output was measured under the conditions of 130% of the standard (2600 rpm, 4.8 kW), with oil temperature and water temperature of 120° C.

TABLE 1

| | Detergent-dispersant | | |
|---|---|---|---|
| | Origin of Alkenyl Group in Imide | Phenols | Acid Treatment |
| Example 1 | polybutene (Mw 987) | Sulfurized Hexadecylphenol | No |
| Example 2 | polybutene (Mw 987) | Sulfurized Hexadecylphenol | No |
| Example 3 | polybutane (Mw 987) | Sulfurized Alkylphenol*[1] | No |
| Example 4 | polybutene (Mw 987) | Sulfurized Dodecylphenol*[3] | No |
| Example 5 | polybutene (Mw 987) | Sulfurized Dodecylphenol*[4] | No |
| Example 6 | polybutene (Mw 987) | Sulfurized Nonylphenol | No |
| Example 7 | polybutene (Mw 800) | Sulfurized Hexadecylphenol | No |
| Example 8 | polybutene (Mw 445) | Sulfurized Hexadecylphenol | No |
| Example 9 | polybutene (Mw 987) | Sulfurized Hexadecylphenol | Boric Acid |
| Example 10 | polydecene (Mw 2038) | Sulfurized Hexadecylphenol | No |
| Example 11 | polydecene (Mw 909) | Sulfurized Hexadecylphenol | No |
| Example 12 | polydecene (Mw 545) | Sulfurized Hexadecylphenol | No |
| Example 13 | polybutene (Mw 987) | Sulfurized Hexadecylphenol | No |
| Example 14 | polybutene (Mw 9B7) | Sulfurized Hexadecylphenol | No |
| Comparative Example 1 | polybutene (Mw 987) | None | No |
| Comparative Example 2 | polybutene (Mw 987) | Hexadecylphenol | No |
| Comparative Example 3 | polybutene (Mw 987) | Sulfurized Phenol | No |
| Comparative Example 4 | polybutene (Mw 987) | Phenol | Glycolic Acid |
| Comparative Example 5 | polybutene (Mw 987) | Sulfurized Alkylphenol*[2] | No |
| Comparative Example 6 | dodecene (Mw 168) | Sulfurized Hexadecylphenol | No |
| Comparative Example 7 | — | Sulfurized Hexadecylphenol | No |
| Comparative Example 8 | polybutene (Mw 987) | Sulfurized Hexadecylphenol | No |

| | Properties of Reaction Product | |
|---|---|---|
| | Base number (mgKOH/g) | Kinematic Viscosity (100° C.)(cSt) |
| Example 1 | 48 | 250 |
| Example 2 | 50 | 234 |
| Example 3 | 42 | 178 |
| Example 4 | 52 | 314 |
| Example 5 | 51 | 1000< |
| Example 6 | 56 | 1000< |
| Example 7 | 54 | 404 |
| Example 8 | 73 | 1000< |
| Example 9 | 45 | 272 |
| Example 10 | 26 | 61 |
| Example 11 | 33 | 97 |
| Example 12 | 49 | 128 |
| Example 13 | 37 | 207 |
| Example 14 | 49 | 258 |
| Comparative Example 1 | 78 | 147 |
| Comparative Example 2 | 60 | 186 |
| Comparative Example 3 | 61 | 1000< |
| Comparative Example 4 | 38 | 1000< |
| Comparative Example 5 | 40 | 165 |
| Comparative Example 6 | 82 | 1000< |
| Comparative Example 7 | 104 | 1000< |

TABLE 1-continued

| | | |
|---|---|---|
| Comparative Example 8 | 56 | 270 |

*[1] Sulfurized Phenol having 20 to 22 carbon atoms
*[2] Sulfurized Phenol having 26 to 28 carbon atoms
*[3] Straight Chain
*[4] Branched Chain

TABLE 2

| | Hot Tube Test (230° C.) | | Panel Coking Test Deposit (mg) | Low Temperature Apparent Viscosity Test (P) |
|---|---|---|---|---|
| | Grade | Deposit (mg) | | |
| Example 1 | 10 | less than 1 | 63 | 57.5 |
| Example 2 | 10 | less than 1 | 55 | 57.0 |
| Example 3 | 8 | less than 1 | 79 | 54.0 |
| Example 4 | 9 | less than 1 | 65 | 57.5 |
| Example 5 | 7 | less than 1 | 75 | 58.0 |
| Example 6 | 6.5 | 2 | 77 | 58.0 |
| Example 7 | 10 | less than 1 | 68 | 48.0 |
| Example 8 | 9 | less than 1 | 69 | 46.0 |
| Example 9 | 10 | less than 1 | 29 | 47.0 |
| Example 10 | 10 | less than 1 | 64 | 39.0 |
| Example 11 | 9 | less than 1 | 66 | 38.5 |
| Example 12 | 8 | less than 1 | 75 | 37.0 |
| Comparative Example 1 | 2 | 25 | 156 | 58.5 |
| Comparative Example 2 | 2 | 23 | 86 | 59.5 |
| Comparative Example 3 | 1.5 | 26 | 119 | 60.0 |
| Comparative Example 4 | 2 | 27 | 111 | 59.5 |
| Comparative Example 5 | 3.5 | 7 | 234 | 58.5 |
| Comparative Example 6*[5] | — | — | — | — |
| Comparative Example 7 | 0 | 30 | 210 | 59.0 |

| | Oxidation Stability Test | | |
|---|---|---|---|
| | Viscosity Ratio | Increase in Total Acid Value (mgKOH/g) | Insoluble Matter (g/100 g) |
| Example 1 | 1.09 | 2.0 | 0.01 |
| Example 2 | 1.12 | 2.2 | 0.04 |
| Example 3 | 1.34 | 3.2 | 0.02 |
| Example 4 | 1.22 | 2.2 | 0.03 |
| Example 5 | 1.36 | 3.0 | 0.07 |
| Example 6 | 1.49 | 3.9 | 0.10 |
| Example 7 | 1.11 | 2.5 | 0.04 |
| Example 8 | 1.23 | 3.3 | 0.05 |
| Example 9 | 1.17 | 3.3 | 0.11 |
| Example 10 | 1.18 | 2.9 | 0.01 |
| Example 11 | 1.24 | 2.9 | 0.04 |
| Example 12 | 1.36 | 3.3 | 0.07 |
| Comparative Example 1 | 3.56 | 27.5 | 5.23 |
| Comparative Example 2 | 3.20 | 25.6 | 3.82 |
| Comparative Example 3 | 1.86 | 10.5 | 0.33 |
| Comparative Example 4 | 4.32 | 17.4 | 2.91 |
| Comparative Example 5 | 2.01 | 9.3 | 0.28 |
| Comparative Example 6*[5] | — | — | — |
| Comparative Example 7 | 1.88 | 8.7 | 2.35 |

*[5] Immiscible with mineral oils

TABLE 3

| | Polybutenyl Succinic Anhydride | | Tetraethylene Pentamine | | Sulfurized Hexadecylphenol | | Paraformaldehyde | |
|---|---|---|---|---|---|---|---|---|
| | (g) | (mol) | (g) | (mol) | (g) | (mol) | (g) | (mol) |
| Example 2 | 69.9 | 0.053 | 9.4 | 0.050 | 35.7 | 0.050 | 3.4 | 0.113 |
| Example 13 | 69.9 | 0.053 | 9.4 | 0.050 | 71.4 | 0.100 | 6.7 | 0.225 |
| Example 14 | 69.9 | 0.053 | 9.4 | 0.050 | 35.7 | 0.050 | 3.4 | 0.113 |
| Comparative Example 8 | 69.9 | 0.053 | 9.4 | 0.050 | 17.9 | 0.025 | 1.7 | 0.056 |

| | Hot Tube Test (230° C.) | | Panel Coking Test |
|---|---|---|---|
| | Grade | Deposit (mg) | Deposit (mg) |
| Example 2 | 10 | less than 1 | 55 |
| Example 13 | 10 | less than 1 | 40 |
| Example 14 | 8.5 | less than 1 | 76 |
| Comparative Example 8 | 2.5 | 6 | 125 |

| | Oxidation Stability Test | | |
|---|---|---|---|
| | Viscosity Ratio | Increase in Total Acid Value (mgKOH/g) | Insoluble Matter (g/100 g) |
| Example 2 | 1.12 | 2.2 | 0.04 |
| Example 13 | 1.04 | 1.7 | 0.00 |
| Example 14 | 1.41 | 3.9 | 0.04 |
| Comparative Example 8 | 2.40 | 12.6 | 0.76 |

| | Hot Tube Test (290° C.) | | Panel Coking Test Deposit (mg) | Simple Diesel Engine Test Period of Durability (hr) |
|---|---|---|---|---|
| | Grade | Deposit (mg) | | |
| Example 15 | 6 | less than 1 | 7 | 86 |
| Example 9 | 0 | 1.3 | 9 | 69 |

| | Oxidation Stability Test | | |
|---|---|---|---|
| | Viscosity Ratio | Increase in Total Acid Value (mgKOH/g) | Insoluble Matter (g/100 g) |
| Example 15 | 1.04 | 1.3 | 0.01 |
| Example 9 | 1.06 | 1.7 | 0.06 |

What is claimed:

1. A Mannich reaction product which is obtained by reacting an alkenyl succinic acid or an alkenyl succinic anhydride with a polyamine containing at least one primary amino group and at least one further primary or secondary amino group; an aldehyde; and a sulfurized alkylphenol represented by the general formula (I):

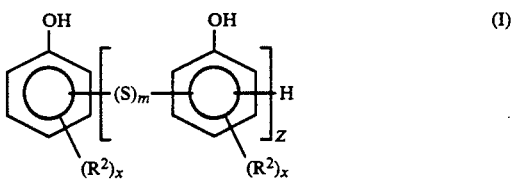

(I)

wherein $R^2$ indicates an alkyl group having 4 to 25 carbon atoms, m indicates an integer of 1 to 8, x indicates 1 or 2, and z indicates an integer of 1 to 9.

2. A process for producing a Mannich reaction product defined in claim 1 which comprises reacting 1 mol or more, to 1 mol of polyamine, of a sulfurized alkylphenol represented by the general formula (I):

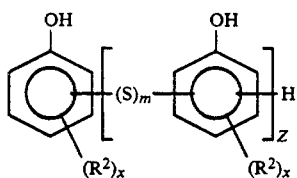

wherein $R^2$ indicates an alkyl group having 4 to 25 carbon atoms, m indicates an integer of 1 to 8, x indicates 1 or 2, and z indicates an integer of 1 to 9.

3. A detergent-dispersant comprising the reaction product defined in claim 1.

4. A lubricating oil composition containing the detergent-dispersant defined in claim 3.

5. A lubricating oil composition for internal-combustion engine which comprises the detergent-dispersant defined in claim 3 and a base oil consisting of at least one oil of a mineral oil and a synthetic oil.

6. A lubricating oil composition for diesel engine which comprises the detergent-dispersant defined in claim 3 and a base oil consisting of at least one oil of a mineral oil and a synthetic oil.

7. A Mannich reaction product which is obtained by reacting an alkenyl succinic acid or an alkenyl succinic anhydride with a polyamine containing at least one primary amino group and at least one further primary or secondary amino group; an aldehyde; a sulfurized alkylphenol represented by the general formula (I):

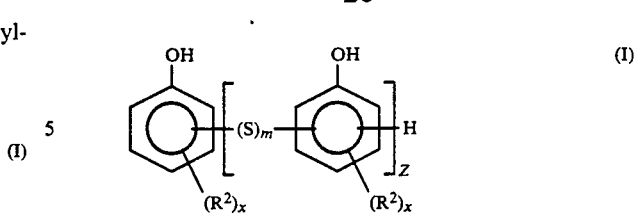

wherein $R^2$ indicates an alkyl group having 4 to 25 carbon atoms, m indicates an integer of 1 to 8, x indicates 1 or 2, and z indicates an integer of 1 to 9, and a born-containing compound.

8. A process for producing a Mannich reaction product defined in claim 7 which comprises reacting 1 mol or more, to 1 mol of polyamine, of a sulfurized alkylphenol represented by the general formula (I):

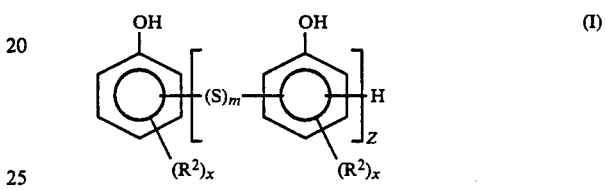

wherein $R^2$ indicates an alkyl group having 4 to 25 carbon atoms, m indicates an integer of 1 to 8, x indicates 1 or 2, and z indicates an integer of 1 to 9.

9. A detergent-dispersant comprising the reaction product defined in claim 7.

10. A lubricating oil composition containing the detergent-dispersant defined in claim 9.

11. A lubricating oil composition for internal-combustion engine which comprises the detergent-dispersant defined in claim 9 and a base oil consisting of at least one oil of a mineral oil and a synthetic oil.

12. A lubricating oil composition for diesel engine which comprises the detergent-dispersant defined in claim 9 and a base oil consisting of at least one oil of a mineral oil and a synthetic oil.

* * * * *